United States Patent [19]
Wilson et al.

[11] Patent Number: 5,165,407
[45] Date of Patent: Nov. 24, 1992

[54] IMPLANTABLE GLUCOSE SENSOR

[75] Inventors: George S. Wilson; Dilbir S. Bindra; Brian S. Hill, all of Lawrence, Kans.; Daniel R. Thevenot, Paris Cedex, France; Robert Sternberg, Thiais, France; Gerard Reach, Paris Cedex, France; Yanan Zhang, Lawrence, Kans.

[73] Assignee: The University of Kansas, Lawrence, Kans.

[21] Appl. No.: 682,560

[22] Filed: Apr. 9, 1991

Related U.S. Application Data

[63] Continuation-in-part of Ser. No. 511,049, Apr. 19, 1990, abandoned.

[51] Int. Cl.$^5$ .............................................. A61B 5/00
[52] U.S. Cl. .................... 128/635; 204/403; 204/415
[58] Field of Search ................. 128/635; 204/403, 415

[56]  References Cited

U.S. PATENT DOCUMENTS

| | | | |
|---|---|---|---|
| 3,249,103 | 5/1966 | Woodhouse | 128/635 |
| 3,726,777 | 4/1973 | Macur | 128/635 X |
| 4,545,382 | 10/1985 | Higgins et al. | 128/635 |
| 4,671,288 | 6/1987 | Gough | 128/635 |

FOREIGN PATENT DOCUMENTS

| | | | |
|---|---|---|---|
| 0320109 | 6/1989 | European Pat. Off. | 128/635 |
| 0169668 | 10/1982 | Japan | 128/635 |
| 60-33644 | 2/1986 | Japan | 128/635 |
| 0261341 | 11/1987 | Japan | 128/635 |
| 0274254 | 11/1987 | Japan | 128/635 |
| 1296913 | 3/1987 | U.S.S.R. | 204/403 |

OTHER PUBLICATIONS

Updike et al., "The Enzyme Electrode", Nature, vol. 214, Jun. 1967, pp. 986-988.
Salkind et al., "Improving... Stability", Med. Inst., vol. 15, No. 2, Mar.-Apr. 1981, pp. 126-127.

Primary Examiner—Lee S. Cohen
Attorney, Agent, or Firm—Hovey, Williams, Timmons & Collins

[57]  ABSTRACT

Implantable enzymatic sensors (25, 43, 44) for biochemicals such as glucose are provided having an ideal size and geometry for optional long term implantation and linear responses over the concentration ranges of interest. The sensors (25, 43, 44) include an elongated body (10, 26, 46) supporting an indicating electrode section having an appropriate enzyme immobilized thereon to present an enzymatic indicating surface (21, 33, 54). A permeable synthetic polymer membrane (24, 42, 56) is applied over the sensor body (10, 26, 46) to protect the enzyme and regulate diffusion of analyte therethrough, to ensure linearity of sensor response. The sensors (25, 43) are of flexible design and can be implanted using a catheter. Alternately, the sensor (44) includes an internal indicating electrode body (46) housed within an apertured, hollow needle (48). A holder (66) affixed to the needle (48) allows for easy manipulation and implantation of the sensor (44).

9 Claims, 3 Drawing Sheets

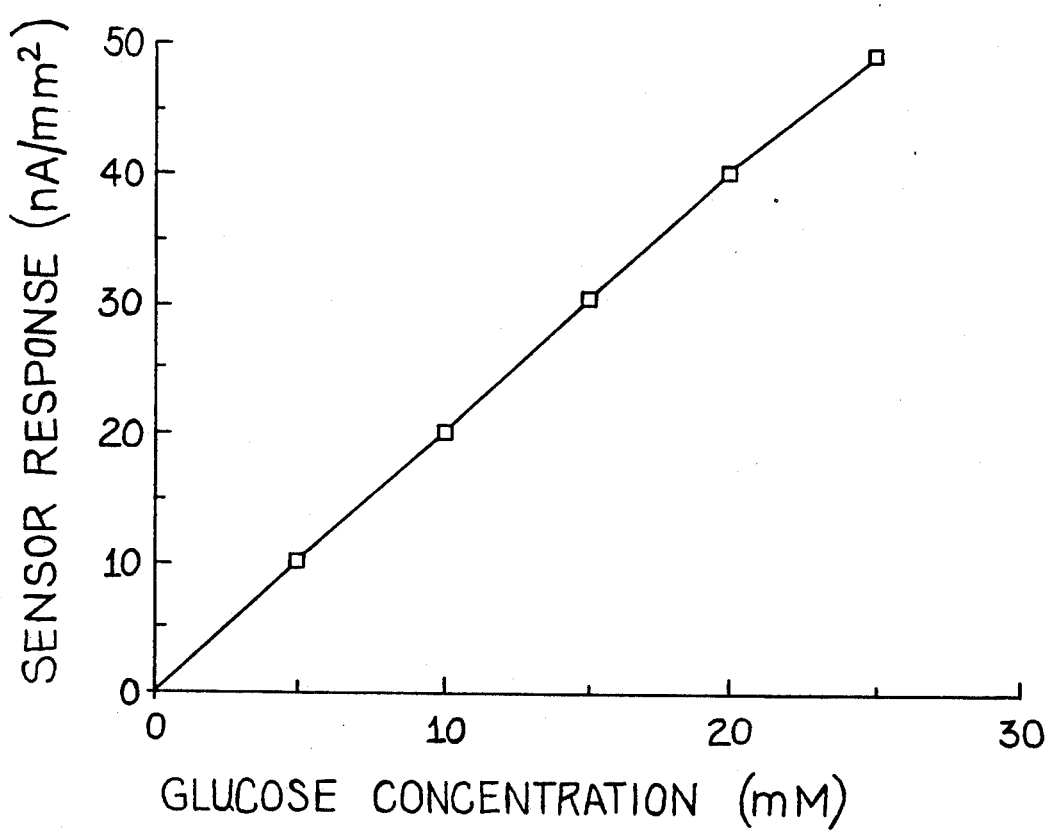
FIG. 3.
FIG. 4.
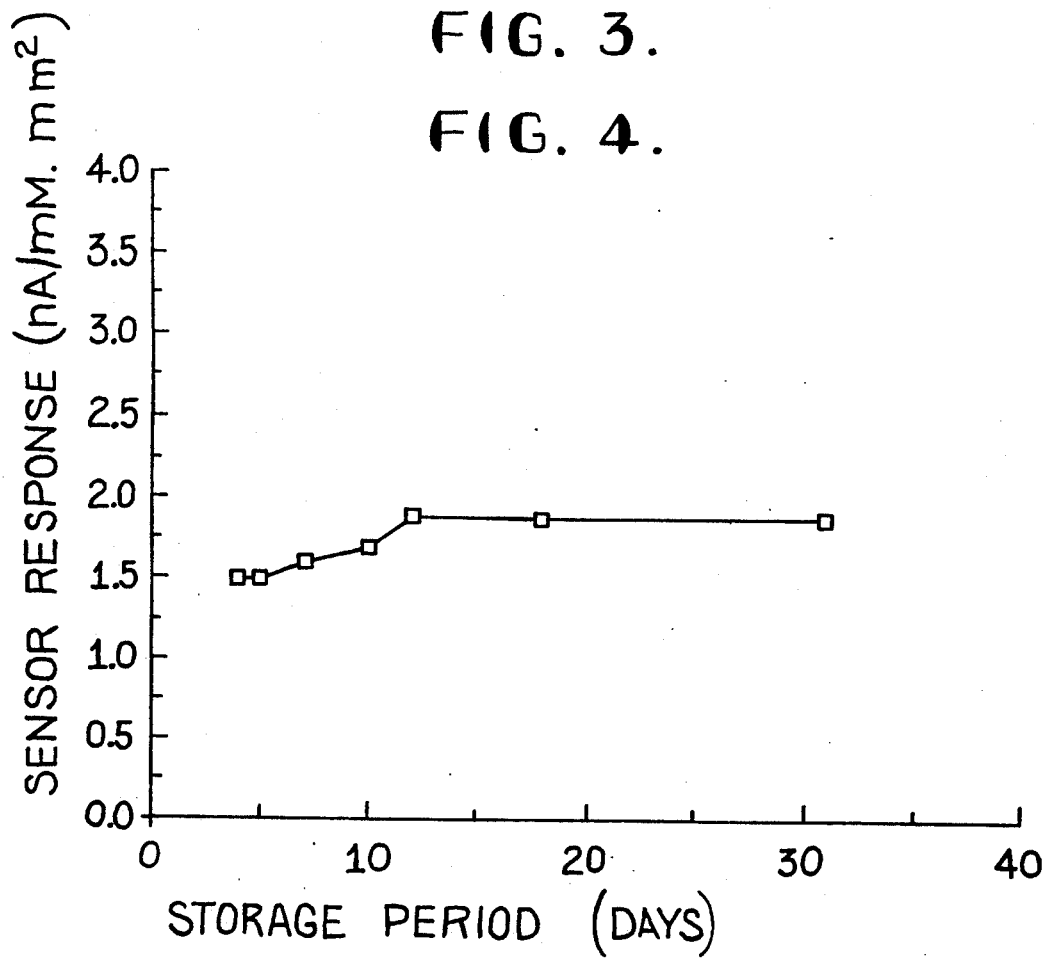

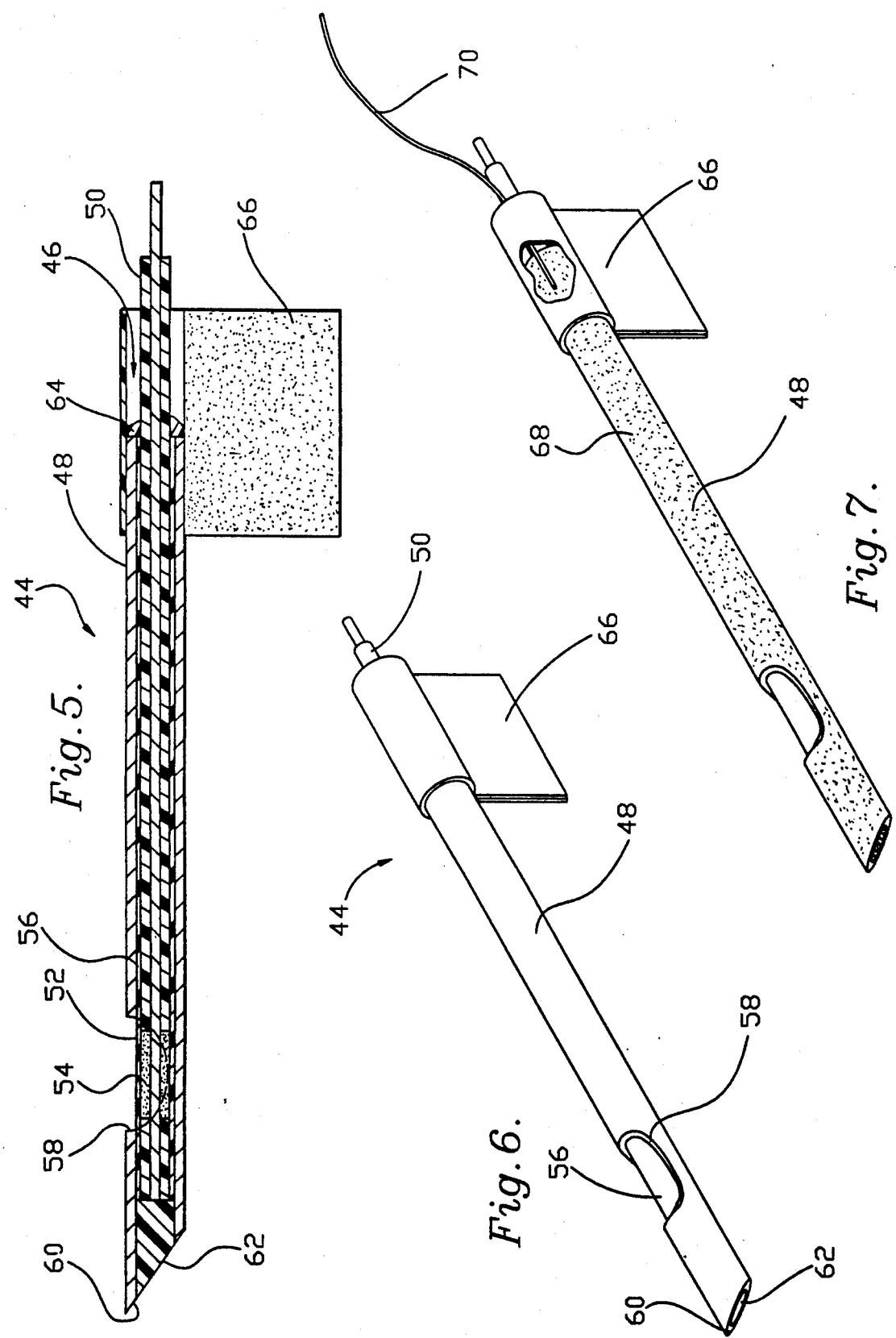

IMPLANTABLE GLUCOSE SENSOR

This is a continuation-in-part of application Ser. No. 07/511,049, filed Apr. 19, 1990, now abandoned.

BACKGROUND OF THE INVENTION

1. Field of the Invention

The present invention is broadly concerned with a subcutaneously implantable enzymatic sensor characterized by small size, optimum geometry and linearity of sensor response over the concentration range of interest. More particularly, it is preferably concerned with an implantable glucose sensor of this type designed to provide, in conjunction with a suitable signal processing unit, a current which is proportional to subcutaneous glucose concentration. In preferred forms, glucose sensors of the invention are based on the enzyme-catalyzed oxidation of glucose to gluconic acid and hydrogen peroxide, the latter being monitored amperometrically by the sensors.

2. Description of the Prior Art

There have been a great many attempts in the past to develop viable implantable sensors for continuous in vivo measurements of biochemicals. For example, considerable effort has been made to devise reliable implantable sensors for monitoring glucose concentrations in blood. Such determinations are useful in a variety of applications, e.g., in the treatment of diabetics. One difficulty in providing a reliable implantable glucose sensor is that glucose levels in the bloodstream of a patient vary on a time basis and are normally dependent upon the physical activity of the individual, his food, beverage and sugar intake, his metabolic rate, and other individualized factors. Furthermore, the geometry of the sensor must be such as to adapt to implantation in a living patient.

Glucose sensors have been proposed in the past which rely upon the well-established enzyme-catalyzed oxidation of glucose wherein glucose and oxygen function as substrates for the enzyme glucose oxidase in the production of gluconic acid and hydrogen peroxide, the latter being monitored amperometrically. See, for example, U.S. Pat. Nos. 3,539,455 to Clark and 4,671,288 to Gough.

Although the idea of an implantable enzymatic glucose sensor is not per se new, considerable difficulty has been encountered in producing reliable, cost-efficient devices of this character. For example, many proposed sensor geometries are simply not realistically implantable, at least for the periods of time required for adequate clinical glucose monitoring. Thus, the devices proposed in the '288 Gough Patent, because of a requirement of multiple electrodes carried within a tubular needle, inevitably are of such diameter as to be uncomfortable to the user and not practical for extended implantation. Furthermore, many prior sensors do not exhibit a stable and linear response, particularly over extended times of implantation, and do not give accurate and reliable results. Finally, fabrication of prior glucose sensors has presented formidable difficulties, to the extent that only about one in five sensors produced by conventional techniques are deemed usable. This obviously represents a considerable inefficiency, to the point that no truly successful implantable glucose sensor has heretofore been produced on a large scale.

SUMMARY OF THE INVENTION

The present invention overcomes the problems outlined above, and provides a greatly improved enzymatic sensor specifically designed for long-term implantation in a patient. The sensor is adapted for positioning in an environment characterized by the presence of biological molecules which are substrates for or products produced by enzymes, in order to determine the presence of such biological molecules. While the principles of the invention may be used in the fabrication of glucose sensors, the invention is not so limited. Indeed, the sensors in accordance with the invention may be produced using a wide variety of immobilized enzymes, for the detection of an equally large number of analytes. Exemplary enzymes and their corresponding substrates are given in U.S. Pat. No. 4,721,677 to Clark, and this patent is incorporated by reference herein.

In any event, the enzymatic sensors in accordance with the invention preferably are in the form of an elongated body supporting at least an indicating electrode, with the indicating electrode presenting a section adapted for exposure to the biological environment. The indicating electrode section has an enzyme operably immobilized thereon to present an enzymatic indicating surface. A number of variants are possible for the reference electrode. For example, use may be made of an externally applied electrocardiogram skin electrode (an 8 mm disk covered with silver chloride and available as Model E-243 from the Phymep Company, 21 Rue Campoformio, Paris, France), or a reference electrode which is implanted with the indicating electrode.

In one specific embodiment employing an implanted reference electrode, the indicating surface of the indicating electrode and the reference electrode are laterally spaced apart along the length of the body and each substantially circumscribes the latter and is substantially exposed to the biological environment when the sensor is placed therein. Use of such circumferentially extending enzymatic indicating surfaces and reference electrodes sections is believed to be an important aspect of this embodiment. Alternately, the reference electrode section may comprise a conductive salt bridge circumscribing the body and lying in a plane transverse to the longitudinal axis of the body; in this case, a reference electrode is placed in electrical contact with the salt bridge, through use of a buffered electrolyte. In another embodiment, the reference electrode is simply placed adjacent the indicating electrode as a part of the overall sensor.

In preferred practice, the sensor body advantageously comprises an electrically conductive noble metal (e.g. platinum or platinum-iridium) electrode covered with electrically insulative material, with a portion of this material removed from the electrode to define an enzyme-receiving zone. Thus, a short length of Teflon (polytetrafluoroethylene) coated platinum-iridium wire may be provided, with a short section of the insulation removed intermediate the ends of the wire, so that respective segments of the insulating material are on opposite sides of and define a recessed enzyme-receiving circumferential zone. Alternately, the endmost portion of the Teflon may be removed, leaving a protruding exposed stretch of wire which defines the enzyme-receiving zone. An enzyme is operably immobilized on the exposed section of the platinum-iridium wire, by known means such as adsorption of the enzyme on a cellulose acetate or Nafion layer (1-3 microns thickness), followed by cross linking with glutaraldehyde.

Another important aspect of the present invention resides in the preferred use of a synthetic polymer membrane disposed over the enzymatic indicating surface to serve as a permeable protective layer. In particular, a layer of polyurethane is advantageously applied as a thin coating over at least the indicating surface (and preferably the entire indicating electrode) in order to protect the enzymatic reaction surface from the biological environment. Moreover, this layer provides a diffusional barrier for glucose which slows down the flow of glucose and creates a linear sensor response over the concentration ranges of interest. In particular, in order to achieve the desired linear response, use is made of an active enzyme layer and a relatively thin protective membrane. It is important that the membrane regulate the passage of molecules therethrough to an extent that the enzymatic reaction between the indicating surface and these molecules is determined by the rate of diffusion through the membrane, and not the enzymatic reaction kinetics. In practice using the methods of sensor construction herein described, an optimal balance between the competing goals of linear response and sensitivity and response times may be achieved.

The use of an additional, negatively charged inner membrane layer immediately adjacent the Pt-Ir wire also retards the diffusion of negatively charged species (e.g. ascorbate and urate) in the biological environment which are interfering species. Of course, this inner membrane does not significantly exclude hydrogen peroxide, and electrically neutral species.

Although the thickness of the outermost polyurethane membrane has not been specifically ascertained, it is estimated that the membrane has a thickness of from about 5 to 10 microns in the preferred glucose sensors hereof.

The sensors described above are, by virtue of their construction, relatively flexible and therefore comfortable in use. However, this same characteristic flexibility makes it necessary to employ a catheter to implant the sensors. In an alternative embodiment, sensors may be provided which can be readily implanted without the need of a catheter, even by the patient himself. In such embodiments, use is made of an elongated, tubular, metallic housing, typically a conventional hypodermic needle; the sensor apparatus is inserted within the needle, and includes an indicating electrode having a section thereof provided with immobilized enzyme. In order to expose the enzyme to the biological environment, the needle sidewall is apertured in registry with the enzyme. A holder is also provided adjacent the rearward end of the needle body in order to facilitate manipulation and insertion of the sensor. This holder advantageously is in the form of a transversely extending flag-like plastic body secured to the needle housing.

The invention also comprehends a novel method of applying the polyurethane membrane described previously. That is to say, a real difficulty in the production of enzymatic sensors stems from the difficulty of applying various materials uniformly to a very small, implantable device. This difficulty has been overcome in the context of the present invention, by applying to the sensor surface a well-defined volume of a polymer dissolved in an organic solvent such that the film is uniformly distributed across the surface. In practice, this method is carried out by providing a wire loop, and holding the coating liquid in the loop by surface tension to form the desired polymer solution droplet, followed by passing the electrodes through the loop to achieve uniform coating along the length of the sensor body.

The enzymatic sensors of the invention have an ideal geometry for implantation. Generally speaking, the flexible units not housed within a needle are equivalent in size and shape to a 26-gauge needle (i.e., about 0.45 mm. outside diameter). Moreover, their geometry permits the reproducible deposition of films and materials and allows careful control of the amount and orientation of the enzyme onto the indicating electrode. Finally, the preferred sensors are effectively "capped" with insulation (Teflon) which prevents the sensors from penetrating further into the tissue than is required. Thus, the insertion of the sensor causes minimal trauma to the tissue and to the sensor itself. The sensor can flex laterally, and this again minimizes tissue damage caused by movement of the patient.

In the case of implantable glucose sensors, response times of less than two minutes and linearities over glucose concentrations of 0-25 mM can be achieved. At the same time, through use of the fabrication techniques of the invention, the rejection rate upon initial manufacture is drastically reduced.

In the case of sensors received within a needle housing, such can be readily manipulated by the patient for implantation purposes. These sensors typically have a slightly larger diameter than the flexible sensors described previously, but are not so large as to cause significant discomfort. This relatively small size is assured because of the sensor construction, making use of a small Teflon-coated Pt-Ir wire and immobolized enzyme.

BRIEF DESCRIPTION OF THE DRAWINGS

FIG. 3 is a graph showing the linear sensor response of the FIG. 1 glucose sensor over a glucose concentration range of 0-25 mM;

FIG. 4 is a graph illustrating the storage stability of the FIG. 1 glucose sensor;

FIG. 5 is a sectional view depicting another sensor embodiment wherein the indicating electrode is housed within an implantable needle;

FIG. 6 is a perspective view of the sensor illustrated in FIG. 5; and

FIG. 7 is a perspective view of an embodiment similar to that of FIG. 6, but depicting the use of an implantable reference electrode.

DESCRIPTION OF THE PREFERRED EMBODIMENTS

Figure 1:
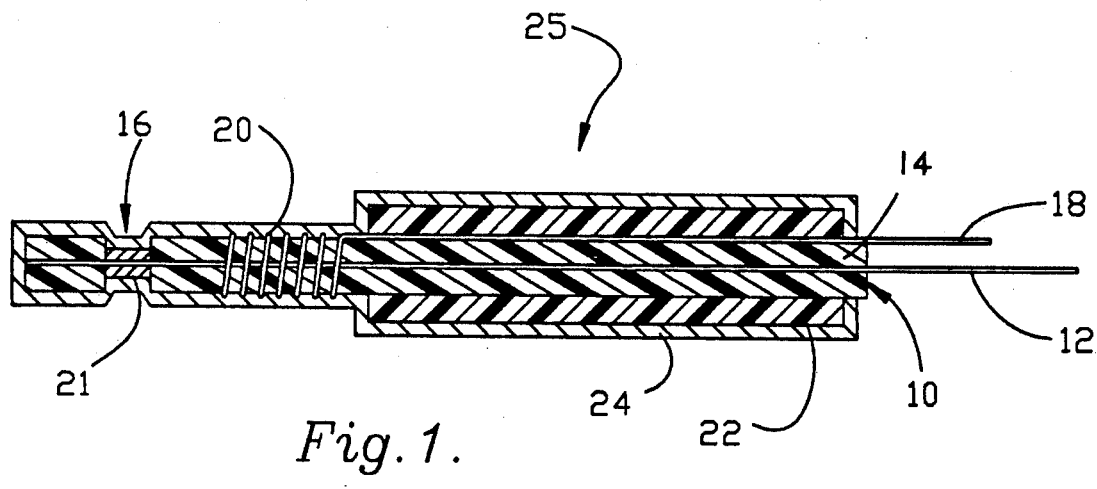
FIG. 1 is an enlarged, sectional view illustrating a glucose sensor in accordance with the invention.
Figure 2:
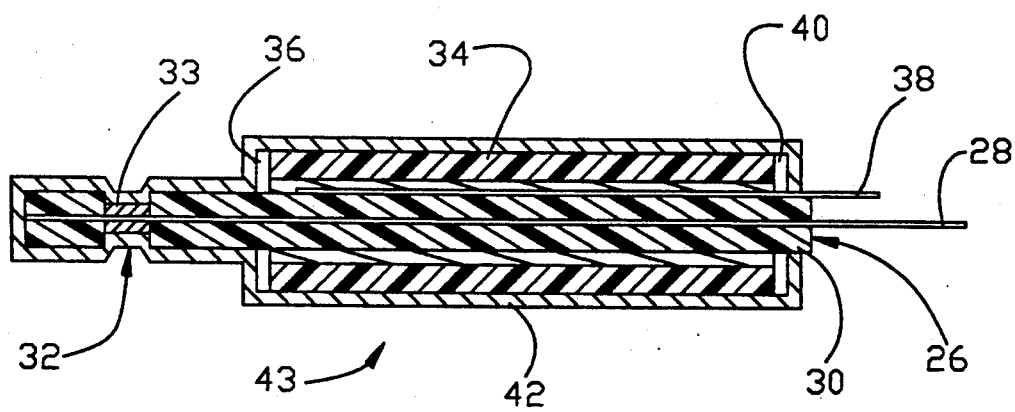
FIG. 2 is an enlarged, sectional view of another glucose sensor in accordance with the invention.

The following examples illustrate the construction of glucose sensors depicted in FIGS. 1 and 2, and are described with particular reference to these drawings. It will be understood, however, that the examples are illustrative only, and nothing therein should be taken as the limitation upon the overall scope of the invention.

EXAMPLE 1-FIG. 1

One end of a 10 cm section 10 of Medwire Corporation Teflon-Coated platinum-iridium wire is provided. The section 10 includes a central platinum-iridium wire 12 (0.18 mm o.d.) and a coating of insulative Teflon 14 (0.035 mm thickness) therearound. The central wire 12 forms the indicating electrode from the sensor. A cavity 16 (1-3 mm in length) is formed in the wire 10 as shown in FIG. 1. This is achieved by first putting a circular cut on the Teflon coating with a paper cutter and then pulling the Teflon out to create a cavity of about 1 millimeter in length, exposing a corresponding section of the wire 12. The excess Teflon extending beyond the left end of the wire 12 is then trimmed off with the cutter.

The reference electrode 18 is formed on the Teflon surface, about 1.5 millimeters to the right of the exposed platinum iridium surface as viewed in FIG. 1. A thin silver wire (0.1 mm o.d., 15 cm length) is tightly wrapped around the TEFLON TM surface covering to form a coil 20 of about 5 millimeters in length. A wire wrapping tool may be utilized for this purpose. The trailing portion of the wire to the right of coil 20 is covered with a section 22 of heat shrinkable Teflon tubing (5 cm long, 1.5 mm o.d., Zeuss Industrial Products Inc.), leaving small lengths of the silver wire and platinum iridium wires uncovered to serve as electrical leads. A heat gun operating at 600° C. is employed for shrinking the Teflon tubing. A layer of silver chloride is formed on the coil 20 by passing current (0.4 mA/cm2) for 60 minutes through the wrapped silver wire while it is dipped in a stirred 0.1N HCL solution. The exposed portions of reference electrode 18 are then rinsed with de-ionized water for 6 hours. The reference electrodes prepared in this manner show a potential of $-64\pm3$ mV (n=10) vs. Ag/AgCl(3M NaCl) in 0.15M NaCl at 37° C.

In order to immobilize glucose oxidase (GOx, E.C.1.1.3.4) on the exposed portion of wire 12, an inner, negatively charged membrane is first applied to the exposed wire section. Thereafter, a circumferentially extending enzymatic indicating layer 21 is formed within cavity 16. Two different approaches have been employed to achieve these ends.

A. Attachment of GOx to Bovine Serum Albumin Coupled Cellulose Acetate

The exposed platinum iridium surface within cavity 16 is degreased by washing with acetone. It is then rinsed with de-ionized water and dried in cold air stream before polymer deposition.

The left hand part of the sensor (portion to the left of the reference electrode coil 20) is dipped into 5% cellulose acetate (39.8% acetyl content) in 50% acetone and 50% ethanol for 10 seconds and is withdrawn slowly. It is then exposed to the vapor above the cellulose acetate solution for 5 seconds and is dipped again into the cellulose acetate solution for 10 seconds. The sensor is then removed and dried in air at room temperature (23° C.) for one minute and placed in deionized water for 6 hours to permit displacement by water of entrapped solvent in the membrane pores. The cellulose acetate membrane prepared in this fashion shows good long-term stability and also discriminates well against ascorbate and urate. Bovine serum albumin (BSA) is then covalently coupled to cellulose acetate and a subsequent reaction of the membrane with GOx, which has previously been activated with an excess of p-benzoquinone, is carried out. The detailed procedure for this reaction is described in the literature, Sternberg et. al., Anal. Chem. 1988, 60, 2781, which is incorporated herein by reference.

B. Physical Adsorption of Enzyme on Cellulose Acetate or Nafion Followed by Crosslinking with Glutaraldehyde 1. The sensor is coated with cellulose acetate in exactly the same manner as described above to create membrane. The GOx (270 U/mg) is physically adsorbed by dropping 5 $\mu$l of GOx solution (40 mg/Ml in 0.1M phosphate buffered saline) on the indicating element within cavity 16, and is allowed to dry for 10 minutes at room temperature. To immobilize the enzyme and form circumferential surface 21, the sensor is exposed to glutaraldehyde vapor generated from 25% glutaraldehyde solution placed at the bottom of an enclosed glass chamber for 12 hours at room temperature. The sensor is then rinsed in de-ionized water and dried in air for 2 hours. The crosslinking with glutaraldehyde protects the enzyme from heat degradation, proteolytic enzymes and hydrolysis, E. M. Salona, C. Saronio, and S. Garattini (eds), "Insolubilized Enzymes." Raven, New York, 1974, incorporated by reference herein.

2. Nafion (Perfluorosulfonic acid polymer, obtained from E. I. DuPont de Nemours and Co., may also be used as an alternate for cellulose acetate for the inner membrane. After cleaning the sensing portion of the sensor as above, it is electrocoated with Nafion using the method described by Adams et al, Neurosci. Meth. Vol. 22, 1987, pp 167-172, incorporated by reference herein. One drop of Nafion (5% solution, Aldrich) is placed in a 2 mm loop formed at one end of a copper wire. A DC potential of $+3$ V is applied to the working electrode with respect to the loop for 10 seconds. The sensor is pulled out of the loop before turning off the potential and is dried in air for 2 hours, and the GOx enzyme is applied as described above.

Alternate polymers may be used in lieu of or in combination with cellulose acetate or Nafion for coating of the exposed Pt-Ir wire surface. For example, polyaniline and polyphenol derivatives can be electrochemically deposited onto the exposed indicating electrode surface. Oxidative electropolymerization of aniline and phenol monomer yields stable and adhesive coating over the exposed wire. These materials moreover have good size selectivity which can be utilized to further improve the sensor selectivity against electrochemical interferences in biological environments. The combination of a size selective coating with a charge selective film (e.g. cellulose acetate) may reduce the in vivo background current and the risk of electrochemical interference. Electropolymerization of aniline and phenol is well known, see for example Ohsaka et al. Anal. Chem. 1987, 59, 1758-61, and Malitesta et al. Anal. Chem. 1990, 62, 2735-40, both of which are incorporated by reference herein.

Finally, Eastman-Kodak AQ 29-D polymer (poly(ester-sulfonic acid)) has both charge and size selective features, and may be applied to the exposed indicating electrode wire in lieu of Nafion. A coating of this type applied to the indicating electrode with a cellulose acetate layer thereover should improve overall selectivity. Combined coatings made from mixtures of cellulose acetate and the AQ 29-D polymer should also provide advantages in terms of sensor selectivity.

In order to complete the preparation of the sensor, the whole assembly, including the reference electrode, is dip coated with 4% polyurethane (Thermedics, SG 85A) dissolved in 98% tetrahydrofuran (THF) and 2% dimethylformamide (DMF) to form an outer membrane 24. The polyurethane solution (10 uL) is held in a wire loop (2 mm i.d.) by surface tension and the sensor is passed through the loop. This leaves a uniform polymer film on the completed sensor 25 to the appropriate extent depicted in FIG. 1. This method provides a good control over the amount of polymer which is applied to the sensor. The sensor is dried in air for 6 hours at room temperature and then left in 0.1M phosphate buffered saline, pH=7.4 for 72 hours for the various outer membranes to condition fully. It is possible to recoat the sensor with polyurethane if the desired linear range of glucose sensitivity is not obtained after the first coating.

EXAMPLE 2—FIG. 2

One end of a 10 cm section 26 of Teflon-coated platinum-iridium wire is provided having a 0.18 mm o.d., a central Pt-Ir wire 28 and a teflon sheath 30 (0.035 mm thickness). The left hand end of the wire is stripped to form a cavity 32 as described in Example 1. The right hand end of section 26 is then inserted into a 5 centimeters long polyethylene tube 34 (0.67 mm o.d., 0.30 mm i.d.). The left hand extremity of the polyethylene tube is sealed by putting a drop of 4% cellulose acetate solution (in acetone) into the opening. The acetone is allowed to dry while holding the Teflon-coated wire in the middle of the polyethylene tube. This permits the formation of a circumferential salt bridge deposit 36 which effectively acts as the terminal part of the reference electrode, lies in a plane transverse to the longitudinal axis of the wire 28 and establishes electrical contact between the reference and sensing electrodes. The empty annular space between the Teflon-coated wire and the polyethylene tube is then filled under vacuum with 0.1M phosphate buffer, pH=7.4 containing 9 g/L NaCl. A chloridized silver wire 38 (0.05 mm o.d., 5 cm long prepared as described in Example 1), is introduced into the polyethylene tube from the right hand end thereof and this opening is also sealed as described above to present a sealing deposit 40. The reference electrode shows a potential of $-60\pm10$ mV (n=6) vs, Ag/AgCl (saturated KCL) at 37° C. The enzyme immobilization and polyurethane deposition steps are then carried out using the procedures described in Example 1 to give the inner, negatively charged membrane 32a, the circumferential indicating enzyme layer 33, and outer permeable membrane 42 illustrated in FIG. 2. The complete sensor 43 is then ready for calibration and use with electrical connections afforded by the axially extending ends of the wires 28, 38.

The sensors described in the above example are calibrated by dipping into a thermostated cell (at 37° C.) containing 10 ml of stirred 0.1M phosphate buffered saline, pH=7.4, and a potential of +600 mV (for hydrogen peroxide detection) is applied between the working and the reference/indicating electrodes. The background current is allowed to stabilized for 20 minutes. The calibration of the sensor is carried out by adding increasing amounts of glucose to the stirred buffer. The current is measured at the plateau (steady state response) and is related to the concentration of the analyte. Following the calibration procedure, the sensors are stored in 0.1M phosphate buffered saline, pH=7.4 at room temperature.

A typical response curve to the glucose addition is shown in FIG. 3, for a sensor made in accordance with FIG. 1. As illustrated, the response characteristics of the sensor over the concentration range of interest (0-25 mM) are essentially linear, and are especially so over the range of 0-15 mM. The sensor output is also essentially independent of the stirring rate. The in vitro characteristics of the sensor are summarized in the following Table. A typical storage stability curve for the sensor is shown in FIG. 4. During the first few days of sensor preparation, the polyurethane membrane changes its permeability for glucose as a result of hydrolytic and swelling processes, leading to the increased passage of glucose and an increased current. After this initial period, however, the stability is excellent.

The sensors of the invention are in use electrically coupled with suitable signal processing equipment, and implanted into a desired subcutaneous site. Glucose and oxygen diffusing through the outer synthetic polymer membrane are enzymatically catalyzed by the $GO_x$ at the indicating surface, resulting in production of gluconic acid and hydrogen peroxide. The latter is measured amperometrically, which is a measurement of glucose concentration.

TABLE

| In Vitro Characteristics of FIG. 1 Glucose Sensor | |
|---|---|
| Parameter | Value |
| Residual current (nA/mm$^2$)$^a$ | 0.7 ± 0.2 |
| Sensitivity (nA/mM · mm$^2$) | 1.8 ± 0.8 |
| Linear Range (upper limit) (mM) | 15 ± 3 |
| Response time (min.), T 90% | 3.5 ± 1 |

Results shown above are expressed as mean ± SD for six sensors.
$^a$Residual currents are measured after 1 hour of polarization.

FIGS. 5 and 6 illustrate another sensor 44 in accordance with the invention. In this case, the sensor body 46 is received within a stainless steel hollow tubular needle 48.

The sensor body 46 includes an innermost, Teflon-coated, platinum-iridium wire 50 (90% Pt/10% Ir) having a total O.D. of about 0.2 mm and a cavity 52 formed therein as described in Example 1. The cavity 52 is approximately 1.0 mm in length and is located about 3.0 mm from the tip of the wire 50. A glucose oxidase layer 54 is immobilized within the cavity 52, and comprises a cellulose acetate polymer layer attached to the surface of the Pt-Ir wire, with glucose oxidase crosslinked through glutaraldehyde onto the cellulose acetate. This procedure is in accordance with Example 1.B.1. above. The entirety of the indicating electrode is then covered by a membrane 56 of polyurethane, again using the method set forth in Example 1.

The sensor body 46 is thereupon inserted into a 25-gauge disposable stainless steel hypodermic needle, the latter having an aperture 58 adjacent the forward, sharpened insertion end 60 thereof. The sensor body 46 is installed in such manner that the glucose oxidase layer 54 comes into registry with the sidewall opening 58, thereby exposing the layer 54 to the biological environment. A silicone rubber plug 62 is installed in the forward end of the needle 48 as shown.

As illustrated in FIG. 5, the wire 50 extends rearwardly out of the end of needle 48, and is adapted to be connected with appropriate instrumentation for measuring glucose concentrations. In order to seal the rearward end of the sensor 44, a bead 64 of epoxy is applied around the wire 50 and the butt end of the needle 48 and sensor body 46.

The overall sensor 44 is completed by provision of a holder 66 extending transversely of the needle 48. The holder 66 is preferably in the form of a plastic sheet wrapped around the rearward end of the needle 48 as shown, and secured by means of epoxy or polycyanoacrylate glue. The holder 66 permits ready manipulation and insertion of the sensor 44 even by the patient.

In the use of sensor 44, the reference electrode may be either externally applied or implanted. As an external electrode, use may be made of a commercial electrocardiogram skin electrode described previously may be used. An external reference electrode should be applied in close proximity to the implanted sensor for the best measurement results. The holder 66 may also be used to support an external electrode of the type described previously. Inasmuch as the holder lies closely adjacent the skin upon implantation, the holder may serve as an ideal platform for the external electrode.

FIG. 7 illustrates an embodiment wherein use is made of an implantable reference electrode. In this case, the needle 48 has an electrodeposited layer 68 of silver on the external surface thereof, with this layer being anodized in the presence of chloride ion to create a Ag-/AgCl reference electrode. A silver lead wire 70 is conductively affixed to the rearward end of needle 48 by means of silver epoxy or similar expedient, and the holder 66 is wrapped about this connection as shown.

Alternately, the inner wall of the stainless steel needle 48 may be provided with an electrodeposited, anodized silver layer, with conducting gel between this layer and the sensor body 46. A silver lead wire would then be conductively secured to the inner needle surface. In this embodiment, electrical current flows through the gel between the indicating electrode and the reference electrode.

Sensors constructed in accordance with FIGS. 5-7, and using either external or implanted reference electrodes, give essentially the same linear response as those constructed in accordance with FIGS. 1-2.

Actual experience with sensors in accordance with the invention has demonstrated that, upon implantation, the cells and capillaries of proximal tissue are slightly damaged. After four or five days, however, such tissues regenerate around the sensor, forming a collagen layer. Neovascularization has also been observed in the collagen layer, and this phenomenon may partially account for the sensitivity of the sensor. This is indicative of operation of the patient's immune system. In any event, the presence of a neovascularized collagen layer adjacent the implanted sensor permits passage of oxygen and glucose. In addition, it has been found that in the first hours after implantation, the sensor response is somewhat variable. Over time, however, this variability is decreased and the performance of the implanted sensor increases. This is believed to be due to the stabilization of the tissue around the implanted sensor. The end result is that the sensors of the present invention may be successfully implanted and left in place for periods of time heretofore thought impractical, e.g., periods of from seven days to three weeks are feasible.

Those skilled in the art will understand that the sensors of the invention may require in vivo calibration. This would typically be done by measuring two blood glucose levels by conventional means, and correlating these known values with the output of the sensor.

It will thus be seen that the enzymatic sensors in accordance with the invention exhibit properties heretofore difficult to achieve, including small, fully implantable size; linearity in response over the concentration ranges of interest; storage stability; and the ability to be consistently manufactured without undue rejection rates.

We claim:

1. A sensor adapted for positioning in an environment characterized by the presence of biological molecules which are substrates for or products produced by enzymes in order to determine the presence of said molecules, said sensor comprising:

an elongated flexible body comprising a length of electrically conductive indicating electrode wire covered with an electrically insulative material, there being a portion of said material removed from said electrode wire to define an enzyme-receiving zone;

an enzyme operably immobilized on said zone to present an enzymatic indicating surface;

a reference electrode supported on said body and presenting a section adapted for exposure to said environment, said indicating surface and said reference electrode section being laterally spaced apart along the length of said body and each substantially circumscribing the body, substantially the entireties of said circumscribing indicating surface and said circumscribing reference electrode section being exposed for reaction with said environment when the sensor is placed therein, said indicating electrode wire serving to support said sensor within said environment without the need for a carrier.

2. The sensor of claim 1, said indicating surface being located intermediate the ends of said length of electrode wire with respective segments of said insulating material being on opposite sides of and defining said enzyme receiving zone.

3. The sensor of claim 1, said reference electrode comprising a coil disposed about said body.

4. The sensor of claim 1, including an outer synthetic polymer membrane disposed over said indicating surface and reference electrode section, said membrane being permeable to said biological molecules.

5. The sensor of claim 4, said membrane being formed of polyurethane.

6. The sensor of claim 4, said membrane having a thickness of from about 5 to 10 microns.

7. The sensor of claim 1, including an inner membrane applied to said electrode wire along the length of said enzyme-receiving zone.

8. The sensor of claim 7, said membrane being negatively charged.

9. The sensor of claim 1, said sensor being a glucose sensor, said enzyme being glucose oxidase.

* * * * *

UNITED STATES PATENT AND TRADEMARK OFFICE
CERTIFICATE OF CORRECTION

PATENT NO. : 5,165,407

DATED : November 24, 1992

INVENTOR(S) : GEORGE S. WILSON, DILBIR S. BINDRA, BRIAN S. HILL, DANIEL R. THEVENOT, ROBERT STERNBERG, GERARD REACH & YANAN ZHANG

It is certified that error appears in the above-indentified patent and that said Letters Patent is hereby corrected as shown below:

Column 1, line 6, before the "Background of the Invention", insert the following paragraph:

--This invention was made with Government support under Grant No. R01 DK 30718 awarded by the National Institutes of Health. The Government has certain rights in the invention.--

Signed and Sealed this

Fourth Day of January, 1994

Attest:

BRUCE LEHMAN

*Attesting Officer*  *Commissioner of Patents and Trademarks*